United States Patent

Belyk et al.

Patent Number: 5,552,521
Date of Patent: Sep. 3, 1996

[54] PROCESS FOR PREPARING CERTAIN AZA CYCLOHEXAPEPTIDES

[75] Inventors: Kevin M. Belyk, Woodbridge; Dean R. Bender, Hazlet; Regina M. Black, Cranford; David L. Hughes, Old Bridge; William Leonard, Watchung, all of N.J.

[73] Assignee: Merck & Co., Inc., Rahway, N.J.

[21] Appl. No.: 386,618

[22] Filed: Feb. 10, 1995

[51] Int. Cl.$^6$ .................................................. C07K 7/64
[52] U.S. Cl. ........................ 530/317; 930/DIG. 546; 930/DIG. 548; 930/270
[58] Field of Search .................... 500/317; 514/11; 930/DIG. 546, DIG. 548, 270

[56] References Cited

U.S. PATENT DOCUMENTS 5,378,804  1/1995  Balkovec et al. .................... 530/317

*Primary Examiner*—Howard Schain
*Attorney, Agent, or Firm*—Elliott Korsen; Mark R. Daniel

[57] ABSTRACT

There is disclosed a novel process for preparing aza cyclohexapeptides of the formula

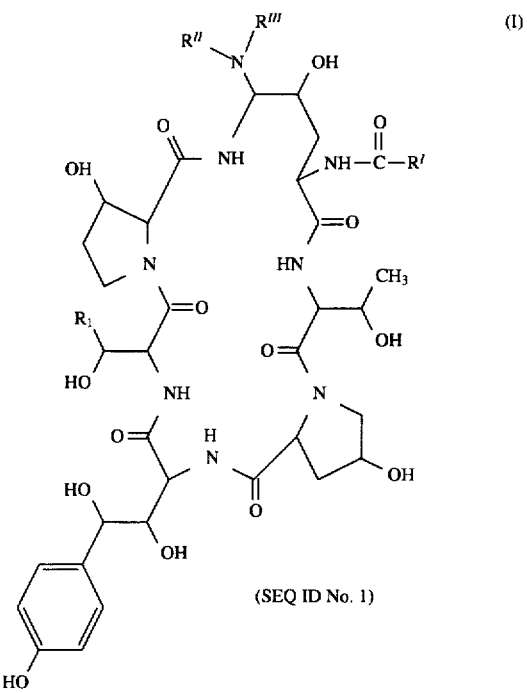

(SEQ ID No. 1)

where all variables are defined herein.

15 Claims, No Drawings

PROCESS FOR PREPARING CERTAIN AZA CYCLOHEXAPEPTIDES

BACKGROUND OF THE INVENTION

This invention relates to an improved process for preparing certain aza cyclohexapeptides of the kind disclosed in U.S. Pat. No. 5,378,804 which issued Jan. 3, 1995. Previously, the process to synthesize these compounds required five steps and was not significantly stereoselective or high yielding. Known reductions of primary amides, such as hydrogenation, metal hydride and electrochemical reduction, require forcing conditions incompatible with the other amides and functional groups in the pneumocandin series. These reductions suffer from lack of chemoselectivity among differently substituted amides. The new process described herein eliminates two steps and results in higher yields and easier synthesis of analogs of the compounds.

SUMMARY OF THE INVENTION

This invention is directed to a process for preparing aza cyclohexapeptides of the formula:

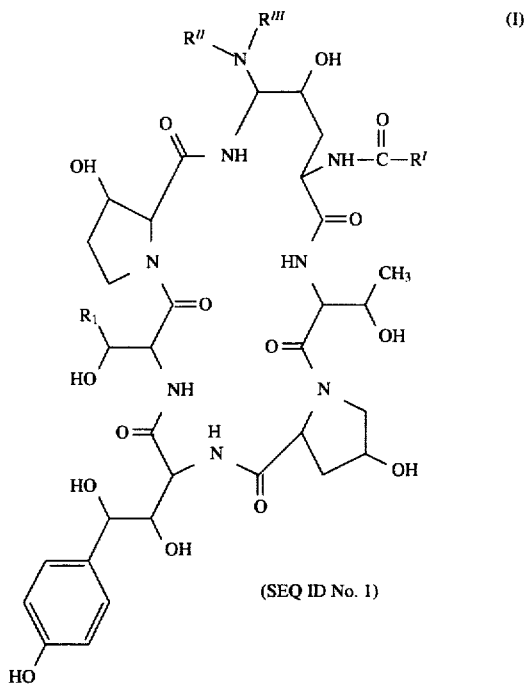

(SEQ ID No. 1)

wherein
$R_1$ is $CH_2CH_2NH_2$ or $CH_2CONH_2$;
$R^I$ is $C_9$–$C_{21}$ alkyl,
  $C_9$–$C_{21}$ alkenyl,
  $C_1$–$C_{10}$ alkoxyphenyl,
  $C_1$–$C_{10}$ alkoxynaphthyl; or
  $C_1$–$C_{10}$ alkoxyterphenyl:
$R^{II}$ is H, $C_1$–$C_4$ alkyl,
  $C_3$–$C_4$ alkenyl,
  $(CH_2)_{2-4}OH$, or
  $(CH_2)_{2-4}NR^{IV}R^V$;
$R^{III}$ is H, $C_1$–$C_4$ alkyl $C_3$–$C_4$ alkenyl, $(CH_2)_{2-4}OH$,
  $(CH_2)_{2-4}NR^{IV}R^V$, or
$R^{II}$ and
$R^{III}$ taken together are $(CH_2)_4$, $(CH_2)_5$, $(CH_2)_2O(CH_2)_2$ or $(CH_2)_2NH(CH_2)_2$;

$R^{IV}$ is H or $C_{1-4}$ alkyl;
$R^V$ is H or $C_1$–$C_4$ alkyl; or
pharmaceutically acceptable acid addition salts thereof.

The compounds prepared by the process of this invention have been found to be useful in treating fungal infections and for the treatment and prevention of infections caused by *Pneumocystis carinii* which are often found in immunocompromised patients such as those suffering with AIDS.

DETAILED DESCRIPTION OF THE INVENTION

This invention relates to a process for preparing compounds of formula (I) through a stereoselective, high yielding process that eliminates two steps from the previous synthetic method.

Throughout the specification and appended claims, a given chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term cycloalkyl refers to a species of alkyl containing from 3 to 15 carbon atoms without alternating or resonating double bonds between carbon atoms.

The term alkenyl refers to groups such as, e.g., vinyl, 1-propene-2-yl, 1-butene-4-yl, 2-buten-4-yl, 1-pentene-5-yl and the like.

The term alkoxy refers to straight or branched chain oxyalkyl groups such as, e.g., methoxy, ethoxy, butoxy, heptoxy, dodecyloxy, and the like.

The compounds of the present invention are generally obtained as mixtures of stereoisomeric forms in which one form usually predominates. Conditions may be adjusted by means within the normal skill of the skilled artisan to obtain predominantly the desired isomer. The compounds with preferred stereoisomeric form designated herein as the "normal" form are those in which the group at the "C-5-orn" position is below the plane at the said position. The designation "epi" has been employed for those compounds in which the group at the "C-5orn" position is above the plane. The "C-5-orn" position is defined as the 5-carbon on the 4-hydroxy ornithine component.

Pharmaceutically acceptable salts suitable as acid addition salts are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in *Journal of Pharmaceutical Science*, 66:2 (1977).

In a preferred embodiment, the process of this invention comprises the steps of reducing Compound II of the formula:

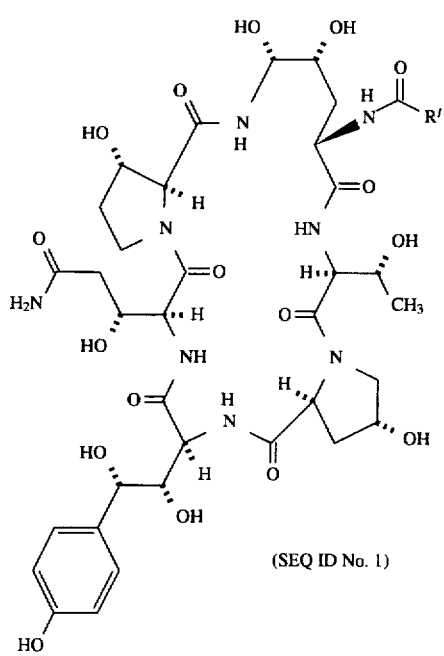
(II)
(SEQ ID No. 1)
to afford Compound III of the formula:
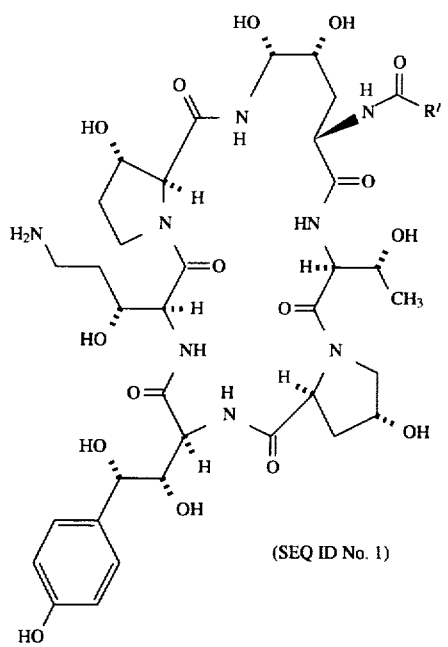
(III)
(SEQ ID No. 1)
which is subsequently converted to Compound IV of the formula:
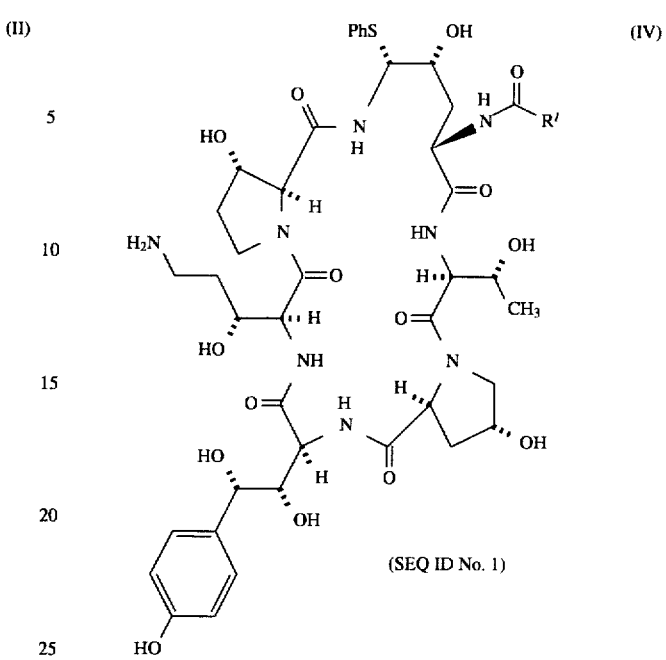
(IV)
(SEQ ID No. 1)
which is stereoselectively converted to Compound I by displacement of the phenylthio group.
In an alternative embodiment, the process comprises the steps of reacting Compound II of the formula:
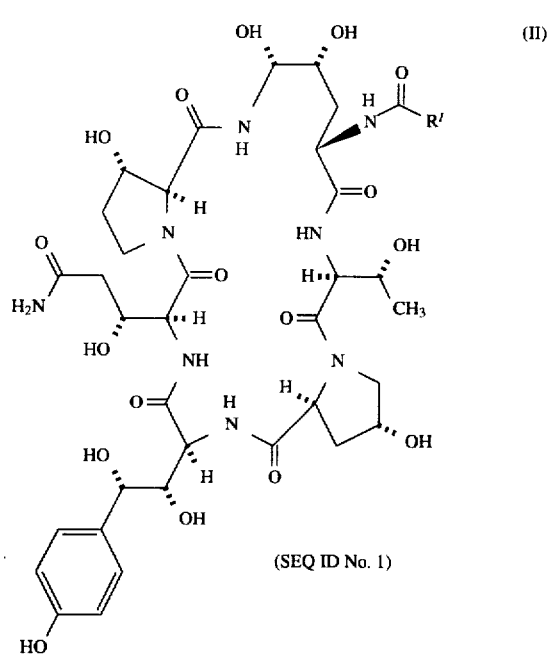
(II)
(SEQ ID No. 1)

with thiophenol to afford Compound IV-a of the formula:

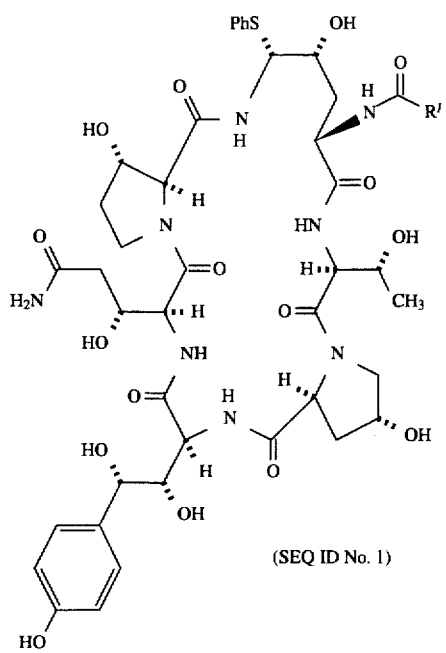

(IV-a) (SEQ ID No. 1)

subsequently reducing Compound IV-a to Compound IV of the formula:

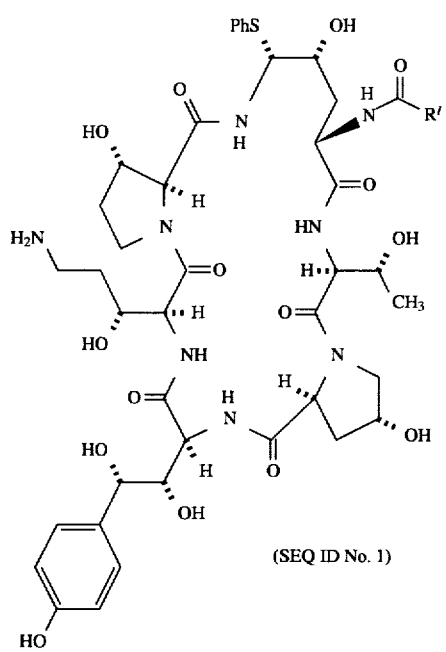

(IV) (SEQ ID No. 1)

which is stereoselectively converted to Compound I by the displacement of the phenylthio group.

Compound II, where $R^1$ is dimethyltridecyl, can be produced by cultivating *Zalerion arboricola* ATCC 20868 in a nutrient medium enriched in mannitol as the primary source of carbon as described in U.S. Pat. No. 5,021,341, issued Jun. 4, 1991.

A preferred compound prepared by the process of the invention is shown below:

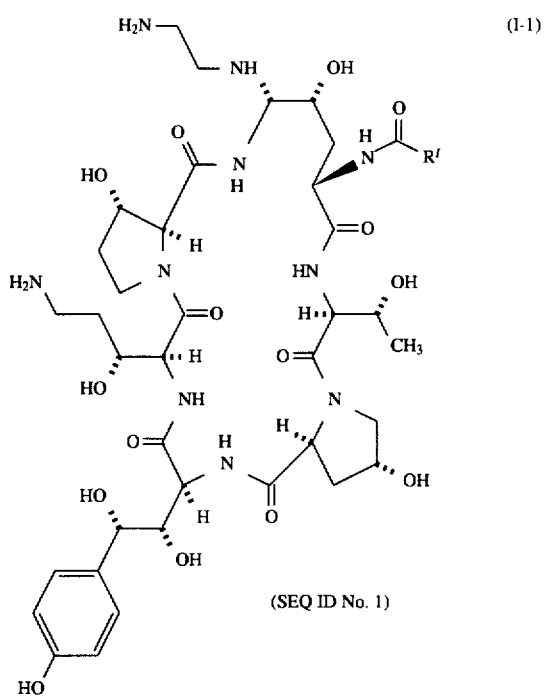

(I-1) (SEQ ID No. 1)

The invention is illustrated in the following steps wherein preferred reactants are shown to more clearly demonstrate the process of the invention. $R'$ is dimethyltridecyl in the following reaction scheme.

REACTION SCHEME

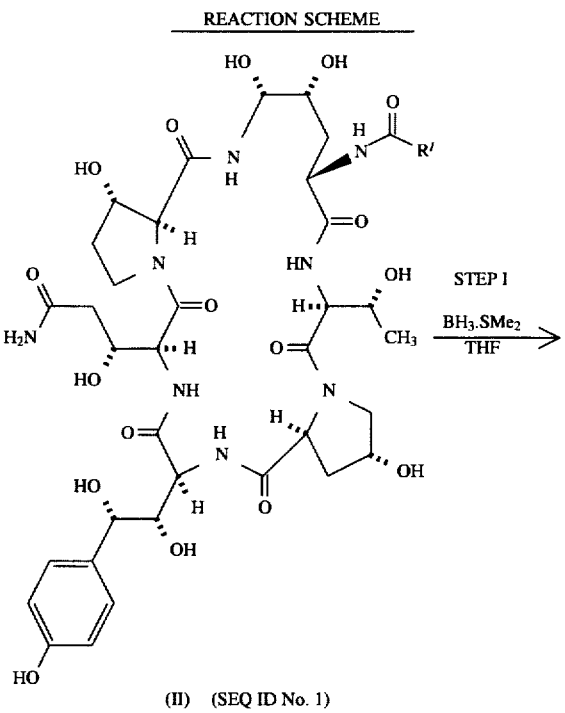

(II) (SEQ ID No. 1)

STEP 1

$BH_3 \cdot SMe_2$
—————→
THF

-continued
REACTION SCHEME

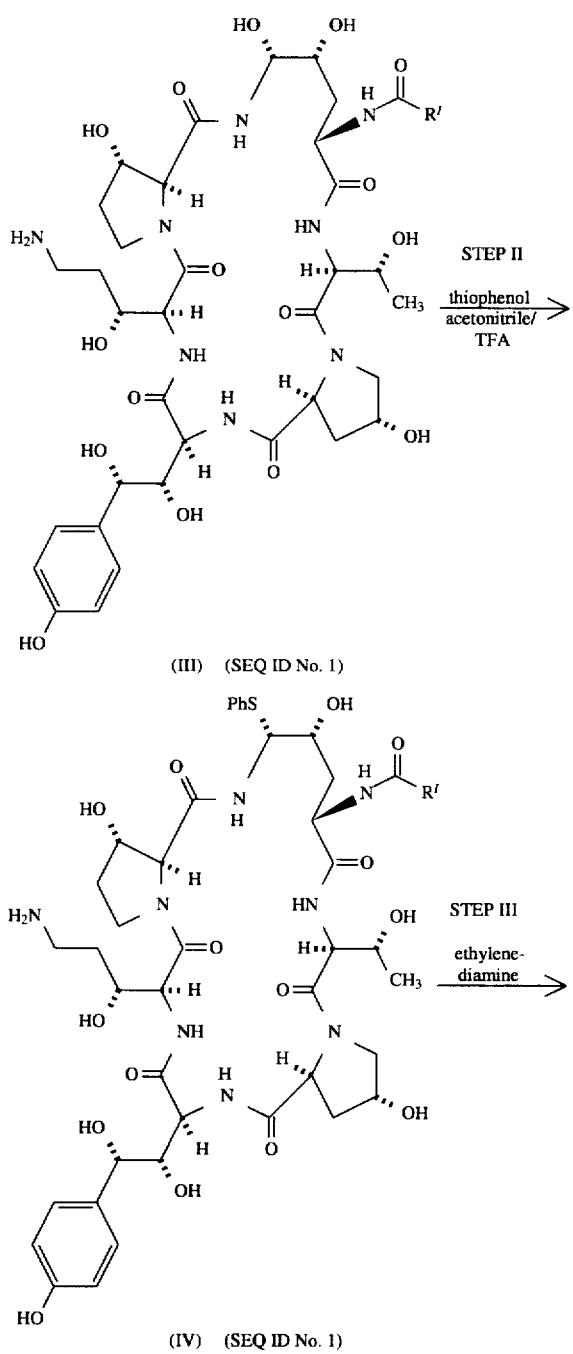

(III)  (SEQ ID No. 1)

(IV)  (SEQ ID No. 1)

STEP II
thiophenol
acetonitrile/
TFA

STEP III
ethylene-
diamine

-continued
REACTION SCHEME

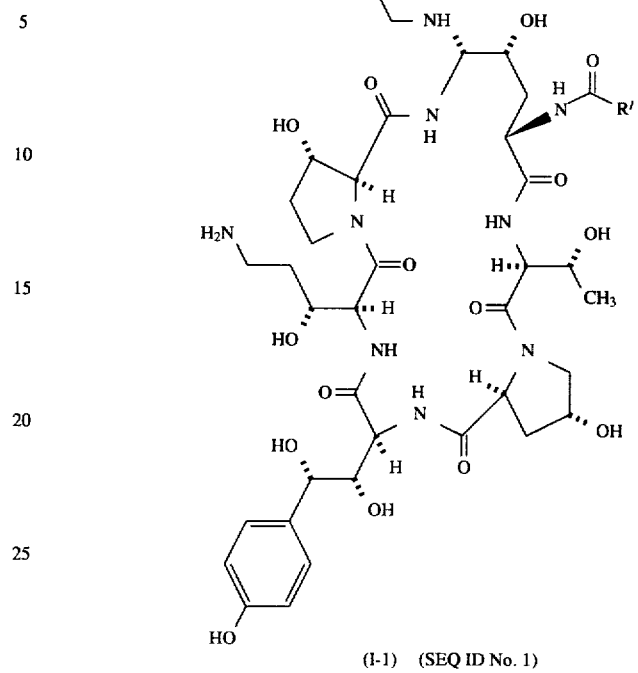

(I-1)  (SEQ ID No. 1)

As shown above, Step 1 involves the reduction of the amide (Compound II) to the amine using a borane complex such as borane with tetrahydrofuran (THF), dimethylsulfide, diphenylsulfide, dibenzylsulfide, 1,4-oxathiane or $BH_2Cl$ with dimethylsulfide or a metal boride such as $ZrCl_4/NaBH_4$ or $TiCl_4/NaBH_4$ in THF or other suitable solvent. The reduction may also be carded out using titanium or zirconium borides or borane complexes with ammonia, dimethylamine, pyridine or piperazine. Preferred reduction agents include the borane complexes with tetrahydrofuran (THF), dimethylsulfide, diphenylsulfide, dibenzylsulfide, 1,4-oxathiane or $BH_2Cl$ with dimethylsulfide or a metal boride such as $ZrCl_4/NaBH_4$ or $TiCl_4/NaBH_4$ in THF or other suitable solvent. Any amide unconverted by this reduction is separated using reverse phase chromatography.

Step II involves the reaction of Compound III with thiophenol in acetonitrile and trifluoroacetic acid (TFA) to produce the phenylsulfide containing intermediate. Any moderate strength acid is expected to produce the intermediate in good yield. Other sulfides such as 4-methoxythiophenol, 2-mercapto-1-methylimidazole and 2-mercaptobenzimidazole may be employed. Compound III is extracted by application of the diluted reaction solution to a reverse phase C-18 column, followed by elution with methanol.

The amount of TFA used is crucial to the rate of displacement as well as to the subsequent formation of the undesired sulfide at the homotyrosine segment of the cyclic peptide. It was found that from about 5–25% TFA in acetonitrile gave the best yield and process aging time with a preferred TFA range of from about 7–15%.

The amount of water to starting material in the reaction mixture was not found to significantly affect the yield.

The amount of thiophenol used in this step is also critical to the yield of the final product. 3 to 5 equivalents provided the best yield.

The preferred conditions for the sulfide formation were determined to be 5 equivalents thiophenol in 10% TFA/acetonitrile at 0° C. These conditions resulted in a yield of 65–70% after solid phase extraction.

Step 3, the displacement of the phenylthio group, bypasses the previous route that went through a sulfone intermediate. The phenylsulfide is reacted in neat ethylenediamine (1:3) at ambient temperature to provide Compound I-1 in 95% yield. The reaction may take place at a temperature of about 10° C. to 40° C. for about 0.5 to 6.0 hours. Preferably the reaction takes place at room temperature for about 1.5 hours. The reaction can also be conducted using ethylenediamine dissolved in a suitable solvent such as water, methanol, ethanol, isopropanol, tetrahydrofuran, trifluoroethanol, dichloroethane or acetonitrile.

The invention is described in greater detail in the following examples in which all pans, preparations, ratios and percentages are by weight unless otherwise indicated. In the example, $R^1$ was dimethyltridecyl.

EXAMPLE 1 a) The synthesis and separation of Compound III from Compound II

Compound II (15.9 g, 89 area % pure, 3.4 wt % water, 0.0128 mol) was added to dry THF (0.64L) and the suspension was dried to <10 mol % water by refluxing through a bed of 3A molecular sieves. Additional dry THF was added to reconstitute the mixture to the original volume and the suspension was cooled to <4° C. with an ice/water/methanol bath.

Neat $BH_3 \cdot SMe_2$ (10.91 g, 0.144 mol) was added over ten minutes and the reaction mixture was maintained at 0°–4° C. The reaction progress was monitored by HPLC until the ratio of starting material to product was 1:1 indicating the end of the reaction age (3.5 h). At 4 hours, the mixture was cooled to –12° C. and slowly quenched with 2N HCl (0.036L). This solution was diluted to 1.14L with water. The assay yield of Compound III was 6.60 g (47%).

The quenched solution was diluted to 4L and loaded onto a medium-pressure column of LiChroprep RP-C18 adsorbent (158 g). After loading, the column was washed with 1.2L water and the amine was eluted with 1.9L of 1:4 v/v acetonitrile/water, and then 0.38L of 1:3 v/v acetonitrile/water.

The rich cuts (>80 area %) were combined and diluted with water to a 1:7.3 v/v acetonitrile/water solution (1.70L total). This mixture was loaded to the same column described above, and the column was washed with 0.57L water. The desired compound was eluted with 0.57L methanol. The rich cut fractions (>85 area %) were combined and concentrated by rotary evaporation and static high vacuum to give 6.81 g (87 wt % pure, 6.8 wt % water) containing 5.92 g of compound III (where $R^1$ is dimethyltridecyl) hydrochloride salt for an isolated yield of 43%.

b) The preparation of the phenylsulfide Compound IV

Compound III (5.80 g assay, 0.00533 mol) was charged to 0.23L of dry acetonitrile and cooled to –5° C. at which point thiophenol (3.10 g, 0.028 mol) was added. TFA (36 g, 24.5 mL, 0.318 mol) was added over 20 minutes in order to keep the temperature of the reaction mixture below 0° C. The reaction was aged at –10° to 0° C. until HPLC analysis showed <3 area % starting material (3.75 h). At this time, chilled water (0.56L) was added slowly (1 h) while cooling the reaction mixture to maintain the temperature below 5° C. The assay yield of the α- and β-phenylsulfide adduct as the trifluoroacetate salt was 4.82 g (71%).

This solution was loaded on the same column described in step a and the column was washed with water (0.57L), then the adsorbed organic compounds were eluted with methanol (0.50L). The rich cuts were concentrated by rotary evaporation and static high vacuum. This yielded 7.20 g (57 wt % pure, 5.1 wt % water) of crude phenylsulfide trifluroacetate salt as an amorphous foamy solid. The corrected isolated step yield for the phenylsulfide was 4.10 g (61%) as a 93:7 mixture of the α- and β-aminal diastereomers.

c) Conversion of the phenylsulfide to the diamine, (Compound I-1)

The crude phenylsulfide trifluoromethanesulfonate salt (8.4 g crude, 57 wt % pure, 0.00377 mole) was added to ethylenediamine (24 mL) while stirring at ambient temperature. The resulting solution was stirred 1.5 h to complete the displacement, then methanol (40 mL) was added followed by acetic acid (45 mL), keeping the temperature below 25° C. with ice-bath cooling. A thick slurry resulted. Water (160 mL) was added to dissolve the slurry, and the aqueous layer was extracted by gentle shaking with hexanes (75 mL). The hexanes layer was back-extracted with water (40 mL) and the combined aq. layer was filtered through a medium-porosity sintered glass funnel, then purified by prep HPLC using a 50 mm diameter C18 column, using 22% acetonitrile/78% 0.15% aq. acetic acid as eluent. The rich cut was lyophilized to provide 4.2 g of 85 wt % pure Compound I-1 as the diacetate salt in 78% isolated step yield.

d) Crystallization of Compound I-1

The solid (2.3 g) was dissolved in ethanol (25 mL) and water (2.7 mL) was then added. The solution was passed through a sintered glass funnel to remove extraneous matter. To this filtrate was added acetic acid (0.14 mL) followed by the slow addition (1.75 h) of ethyl acetate (14 mL). The solution was seeded and the seed bed was aged for 1 h. The remaining ethyl acetate (32 mL) was added over 5 h and aged an additional 1 h. The crystalline solid was collected on a sintered-glass funnel and washed with a solution of ethanol/ethyl acetate/water (6 mL/9 mL/0.5 mL, respectively). The wet cake was dried with a nitrogen flow to give 1.91 g (1.75 assay g, 88% recovery) of the diacetate salt of compound I-1.

What is claimed is:

1. A process for preparing aza cyclohexapeptide compounds of the formula

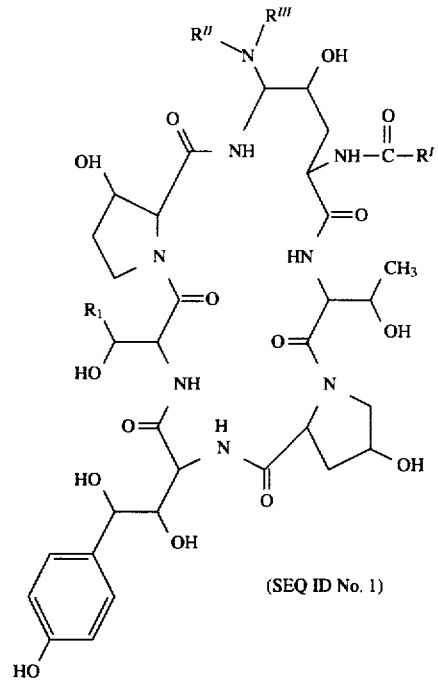

(SEQ ID No. 1)

wherein $R_1$ is $CH_2CH_2NH_2$ or $CH_2CONH_2$;

$R'$ is $C_9$–$C_{21}$ alkyl,
$C_9$–$C_{21}$ alkenyl,
$C_1$–$C_{10}$ alkoxyphenyl,
$C_1$–$C_{10}$ alkoxynaphthyl, or
$C_1$–$C_{10}$ alkoxyterphenyl:

$R''$ is H, $C_1$–$C_4$ alkyl,
$C_3$–$C_4$ alkenyl,
$(CH_2)_{2-4}OH$, or
$(CH_2)_{2-4}NR^{IV}R^V$;

$R'''$ is H, $C_1$–$C_4$ alkyl $C_3$–$C_4$ alkenyl, $(CH_2)_{2-4}OH$, $(CH_2)_{2-4}NR^{IV}R^V$, or $R''$ and $R'''$ taken together are $(CH_2)_4$, $(CH_2)_5$, $(CH_2)_2O(CH_2)_2$ or $(CH_2)_2NH(CH_2)_2$;

$R^{IV}$ is H or $C_1$–$C_4$ alkyl;

$R^V$ is H or $C_1$–$C_4$ alkyl; or pharmaceutically acceptable acid addition salts thereof which comprises the steps of a) reducing Compound H of the formula

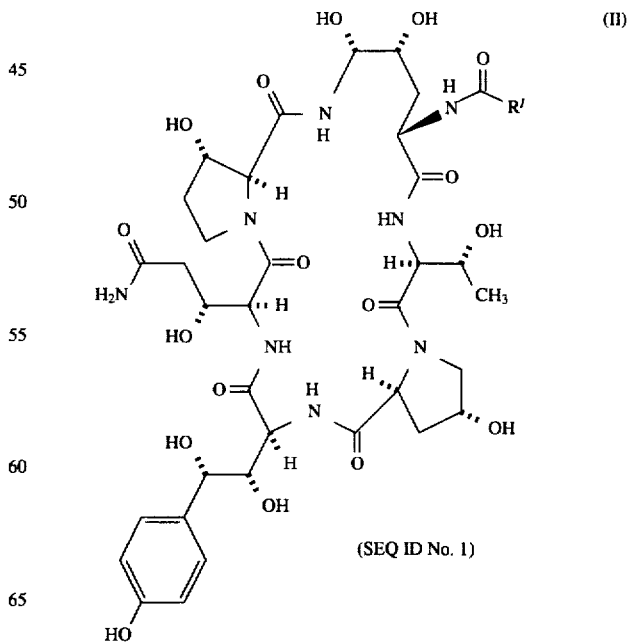

(SEQ ID No. 1)

to afford Compound III of the formula

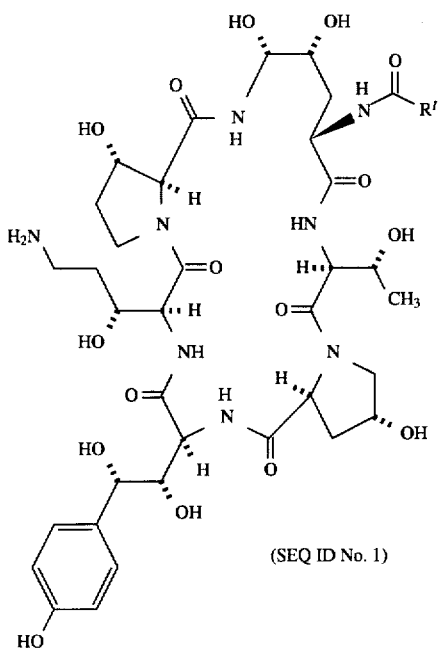

(SEQ ID No. 1)

b) converting Compound III to afford Compound IV of the formula

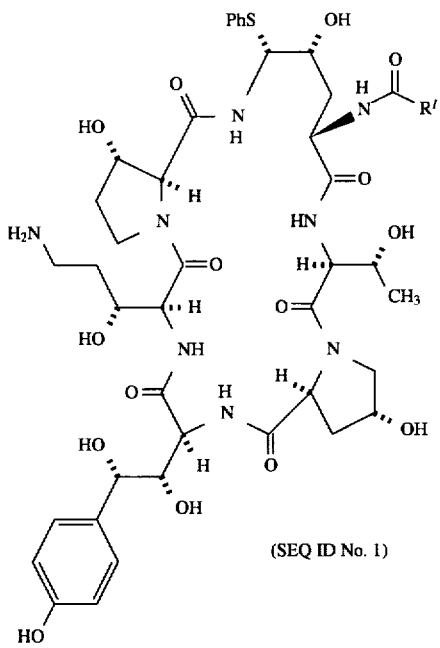

(SEQ ID No. 1)

and, c) stereoselectively converting Compound IV to Compound I by the displacement of the phenylthio group.

2. The process of claim 1 wherein the reduction in Step (a) is accomplished using a borane complex or metal boride.

3. The process of claim 2 wherein the metal boride is $ZrCl_4/NaBH_4$ or $TiCl_4/NaBH_4$ and the borane complex is borane complexed with dimethylsulfide, dibenzylsulfide, diphenylsulfide, THF or 1,4-oxathiane or $BH_2Cl$ with dimethylsulfide.

4. The process of claim 1 wherein Compound III is converted to the phenylsulfide by reaction with thiophenol in a suitable solvent.

5. The process of claim 4 wherein the suitable solvent is acetonitrile.

6. The process of claim 1 where the displacement of the phenylthio group takes place in neat ethylenediamine or with ethylenediamine dissolved in a suitable solvent at a temperature of about 10° C. to 40° C.

7. The process of claim 6 wherein the suitable solvent is selected from water, methanol, ethanol, tetrahydrofuran, isopropanol, trifluoroethanol, acetonitrile or dichloromethane.

8. A process for preparing aza cyclohexapeptide compounds of the formula

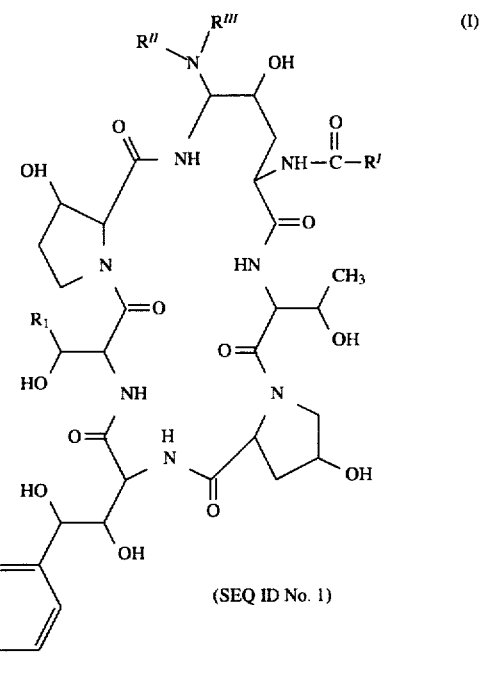

(SEQ ID No. 1)

wherein $R_1$ is $CH_2CH_2NH_2$ or $CH_2CONH_2$;

$R_I$ is $C_9$–$C_{21}$ alkyl, $C_9$–$C_{21}$ alkenyl, $C_1$–$C_{10}$ alkoxyphenyl, $C_1$–$C_{10}$ alkoxynaphthyl, or $C_1$–$C_{10}$ alkoxyterphenyl:

$R''$ is H, $C_{1-4}$ alkyl, $C_3$–$C_4$ alkenyl, $(CH_2)_{2-4}OH$, or $(CH_2)_{2-4}NR^{IV}R^V$; or $R'''$ is H, $C_1$–$C_4$ alkyl $C_3$–$C_4$ alkenyl, $(CH_2)_{2-4}OH$, $(CH_2)_{2-4}NR^{IV}R^V$, or $R''$ and $R'''$ taken together are $(CH_2)_4$, $(CH_2)_5$, $(CH_2)_2O(CH_2)_2$ or $(CH_2)_2NH(CH_2)_2$;

$R^{IV}$ is H or $C_1$–$C_4$ alkyl;

$R^V$ is H or $C_1$–$C_4$ alkyl; or pharmaceutically acceptable acid addition salts thereof which comprises the steps of a) reacting Compound II of the formula

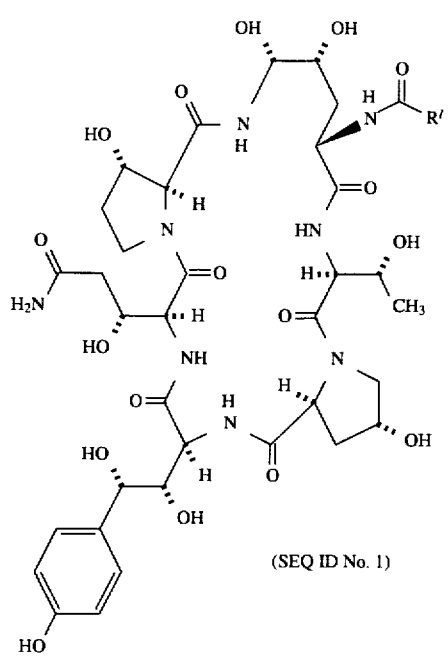

(SEQ ID No. 1)

with thiophenol to afford Compound IV-a of the formula

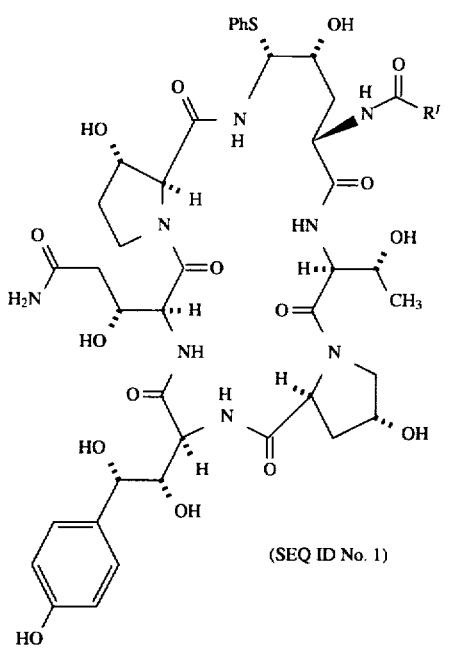

(SEQ ID No. 1)

b) reducing Compound IV-a to afford Compound IV of the formula

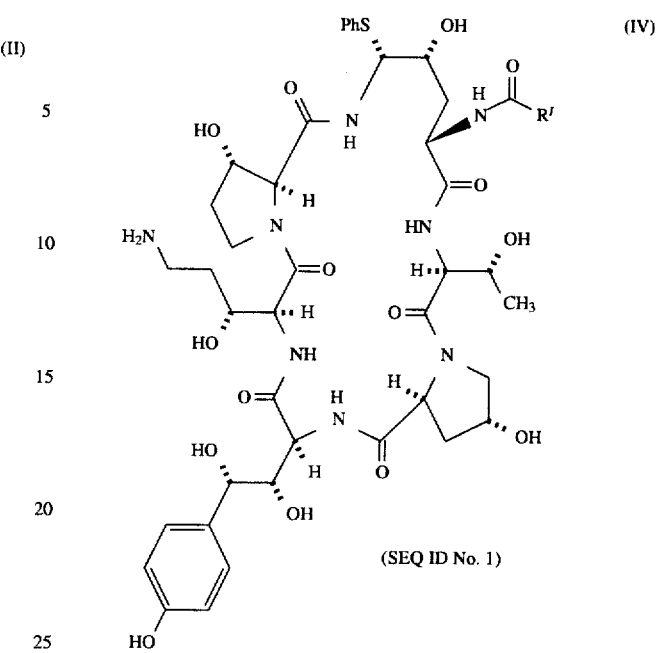

(SEQ ID No. 1)

and, c) stereoselectively converting Compound IV to Compound I by the displacement of the phenylthio group.

9. The process of claim 8 wherein the reduction in Step (b) is accomplished using a borane complex or metal boride.

10. The process of claim 9 wherein the metal boride is $ZrCl_4/NaBH_4$ or $TiCl_4/NaBH_4$ and the borane complex is borane complexed with dimethylsulfide, dibenzylsulfide, diphenylsulfide, THF or 1,4-oxathiane or $BH_2Cl$ with dimethylsulfide.

11. The process of claim 8 wherein Compound II is converted to the phenylsulfide by reaction with thiophenol in a suitable solvent.

12. The process of claim 11 wherein the suitable solvent is acetonitrile.

13. The process of claim 8 where the displacement of the phenylthio group takes place in neat ethylenediamine or with ethylenediamine dissolved in a suitable solvent at a temperature of about 10° C. to 40° C.

14. The process of claim 13 wherein the suitable solvent is selected from water, methanol, ethanol, tetrahydrofuran, isopropanol, trifluoroethanol, acetonitrile or dichloromethane.

15. The process of claim 1 wherein a compound of the formula

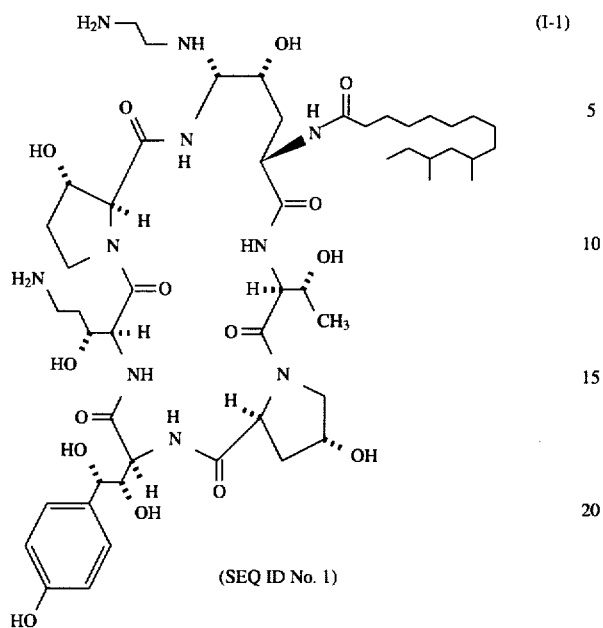
(I-1)
(SEQ ID No. 1)
is prepared.
* * * * *

UNITED STATES PATENT AND TRADEMARK OFFICE
CERTIFICATE OF CORRECTION

PATENT NO. : 5,552,521
DATED : September. 3, 1996
INVENTOR(S) : Kevin M. Belyk, Dean R. Bender, Regina M. Black, David L. Hughes, William Leonard.

It is certified that error appears in the above-indentified patent and that said Letters Patent is hereby corrected as shown below:

In the Claims:

Col. 12, Claim 1, line 41, delete "H" and insert in its place -- II --.

Signed and Sealed this

Tenth Day of December, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa Thr Xaa Xaa Xaa Xaa
1             5